(12) United States Patent  
Csizmadia (10) Patent No.: US 9,079,009 B2  
(45) Date of Patent: Jul. 14, 2015

(54) METHOD AND APPARATUS FOR TREATMENT OF PATHOGENS INCLUDING VIRUSES AND BACTERIA

(76) Inventor: Paul Csizmadia, Leanyer (AU)

( * ) Notice: Subject to any disclaimer, the term of this patent is extended or adjusted under 35 U.S.C. 154(b) by 0 days.

(21) Appl. No.: 14/237,530

(22) PCT Filed: Aug. 8, 2012

(86) PCT No.: PCT/AU2012/000934  
§ 371 (c)(1),  
(2), (4) Date: Feb. 6, 2014

(87) PCT Pub. No.: WO2013/023239  
PCT Pub. Date: Feb. 21, 2013

(65) Prior Publication Data  
US 2014/0207026 A1 Jul. 24, 2014

(30) Foreign Application Priority Data  
Aug. 12, 2011 (AU) ................. 2011903234

(51) Int. Cl.  
*A61H 1/00* (2006.01)  
*A61N 7/00* (2006.01)  
*A61H 23/02* (2006.01)  
*A61H 33/00* (2006.01)

(52) U.S. Cl.  
CPC . *A61N 7/00* (2013.01); *A61H 23/02* (2013.01); *A61H 23/0245* (2013.01); *A61H 33/0087* (2013.01); *A61H 33/60* (2013.01)

(58) Field of Classification Search  
CPC ........... A61H 23/0245; A61H 33/0087; A61H 33/60; A61H 7/00  
USPC ............... 600/407, 437, 441; 601/1, 2  
See application file for complete search history.

(56) References Cited

U.S. PATENT DOCUMENTS

2006/0106424 A1 5/2006 Bachem  
2010/0113983 A1 5/2010 Heckerman et al.

FOREIGN PATENT DOCUMENTS

WO 2006114638 A2 11/2006  
WO 2010009141 A1 1/2010

OTHER PUBLICATIONS

International Search Report for PCT/AU2012/000934, completed by the Australian Patent Office on Sep. 28, 2012, 3 Pages.

*Primary Examiner* — Unsu Jung  
*Assistant Examiner* — Joel Lamprecht  
(74) *Attorney, Agent, or Firm* — Brooks Kushman P.C.

(57) ABSTRACT

A method for disrupting or destroying selected pathogens located within the body of an organism the method including the non-invasive administration to pre-selected locations on or in the organism of an amount of low intensity ultrasonic energy, effective to disrupt or destroy the selected pathogens but not deleteriously affect the organism, the low intensity ultrasonic energy falling within predefined ranges of frequencies, wherein the predefined range of frequencies is one or more ranges of frequencies at which the low intensity ultrasonic energy has optimal effectiveness in disrupting or destroying a particular pathogen, and the intensity of the low intensity ultrasonic energy falling within predefined ranges of intensity, wherein the predefined range of intensity of low intensity ultrasonic energy is such as to allow for disruption or destruction of the selected pathogens but not deleteriously affect tissue of the organism surrounding the selected pathogens.

10 Claims, 3 Drawing Sheets

Power Calibration at 3.6W

| freq (kHz) | Terminal Voltage (Volts pk-pk) | Acoustic power (W) | Equivalent intensity (mW/cm^2) |
|---|---|---|---|
| 260 | 0.66 | 3.7 | 31.2 |
| 265 | 0.64 | 3.4 | 28.6 |
| 270 | 0.62 | 3.7 | 31.1 |
| 275 | 0.56 | 3.5 | 29.2 |
| 280 | 0.56 | 3.6 | 29.9 |
| 285 | 0.5 | 3.5 | 29.2 |
| 290 | 0.5 | 3.6 | 30.3 |
| 295 | 0.5 | 3.8 | 31.7 |
| 300 | 0.495 | 3.9 | 32.3 |
| 305 | 0.45 | 3.4 | 28.6 |
| 310 | 0.51 | 3.5 | 29.1 |
| 315 | 0.525 | 3.3 | 27.4 |
| 320 | 0.54 | 3.3 | 27.4 |
| 325 | 0.6 | 3.6 | 29.9 |
| 330 | 0.64 | 3.4 | 28.6 |
| 335 | 0.68 | 3.3 | 27.4 |
| 340 | 0.78 | 3.4 | 28.6 |
| 345 | 0.85 | 3.5 | 29.2 |
| 350 | 0.9 | 3.7 | 31.1 |
| 355 | 0.93 | 3.6 | 29.9 |
| 360 | 0.96 | 3.6 | 29.9 |
| 365 | 0.96 | 3.3 | 27.4 |
| 370 | 1 | 3.7 | 30.5 |
| 375 | 1.01 | 3.5 | 29.4 |
| 380 | 1.04 | 3.4 | 28.6 |

*FIG. 3*

Power Calibration at 7.8W

| freq (kHz) | Terminal Voltage (Volts pk-pk) | Acoustic power (W) | Equivalent intensity (mW/cm^2) |
|---|---|---|---|
| 260 | 0.86 | 7.8 | 64.7 |
| 265 | 0.86 | 7.6 | 63.4 |
| 270 | 0.86 | 7.9 | 65.9 |
| 275 | 0.84 | 7.9 | 65.9 |
| 280 | 0.76 | 7.7 | 64.1 |
| 285 | 0.73 | 7.6 | 63.4 |
| 290 | 0.73 | 8.1 | 67.2 |
| 295 | 0.71 | 8.2 | 68.4 |
| 300 | 0.69 | 7.8 | 64.7 |
| 305 | 0.69 | 7.9 | 65.9 |
| 310 | 0.71 | 7.6 | 63.4 |
| 315 | 0.76 | 7.6 | 63.4 |
| 320 | 0.8 | 7.5 | 62.8 |
| 325 | 0.89 | 7.5 | 62.8 |
| 330 | 0.95 | 7.6 | 63.4 |
| 335 | 1 | 7.9 | 65.9 |
| 340 | 1.06 | 7.9 | 65.9 |
| 345 | 1.2 | 7.8 | 64.7 |
| 350 | 1.3 | 7.8 | 64.7 |
| 355 | 1.35 | 7.8 | 64.7 |
| 360 | 1.4 | 8.1 | 67.2 |
| 365 | 1.45 | 8.0 | 66.5 |
| 370 | 1.46 | 7.8 | 64.7 |
| 375 | 1.57 | 8.2 | 68.4 |
| 380 | 1.53 | 7.7 | 63.8 |

FIG. 4

METHOD AND APPARATUS FOR TREATMENT OF PATHOGENS INCLUDING VIRUSES AND BACTERIA

CROSS-REFERENCE TO RELATED APPLICATION

This application is the U.S. national phase of PCT Application No. PCT/AU2012/000934 filed on Aug. 8, 2012, which claims priority to Australian Patent Application No. 2011903234 filed on Aug. 12, 2011, the disclosures of which are incorporated in their entirety by reference herein.

FIELD OF THE INVENTION

This invention relates to a method/process and apparatus for a non-invasive treatment of micro-organisms/pathogens within a host's body or outside a host's body, the host being either human or animal. In particular it relates to a method/process and apparatus for treatment of micro-organisms/pathogens in both the bacterial and viral groups. More particularly it relates in one form to treatment of Herpes Simplex I and II viruses but is not limited to such. In another form, the invention relates to treatment of *Staphylococcus Aureus* bacteria.

BACKGROUND TO THE INVENTION

Generally the most common way to kill invading organisms involved in infection of a host is exposure to specific chemicals, which interfere in their metabolism without substantially deleteriously affecting the host. These chemicals could include antibiotics and antivirals and are in wide use.

However some organisms such as viruses live inside the cells and are not treatable with antibiotics. Further, some infections present in those tissues which have poor blood supply can result in a chronic deep-seated infection for example osteomyelitis. Further, if the host's immune system is compromised, such as in some cases of HIV then usually mild infections can spread rapidly. Still further, many bacteria have developed a resistance to the commonly used antibiotics.

In general, many different micro-organisms can invade a host, including the human body, and reside there. Some can cause only mild problems and eventually are destroyed by the host's immune system—others can cause recurring problems or kill the host. Various treatments have been devised to treat these organisms such as antiseptics, antibiotics or antivirals. Several factors can affect the efficacy of treatment such as:
 Site of infection (poor blood supply)
 Nature of organism i.e. does it exist outside cells where antibiotics can reach it or
 Some organisms such as viruses reside within the host cells and cannot be reached
 Development of resistance to antibiotics.

Herpes viruses living inside the body cells are difficult to destroy without harming the host. When the virus is first transmitted in the case of genital herpes—usually via sexual contact—it causes a reaction in the skin consisting of painful blisters.

These eventually heal but the virus particles are not destroyed by the 'immune system'. Instead they migrate to the bottom of the spine into clumps of nerve cells called the dorsal ganglia. The dormant virus particles can stay there indefinitely and at times of physical or emotional stress they travel back down the nerves to approximately the same area of skin to cause further blistering. This cycle can repeat indefinitely.

OBJECT OF THE INVENTION

It is an object of the invention to provide a method/process and apparatus for treating pathogens within a human or animal body without substantially damaging the host.

It is also an object of the invention to provide a method/process and apparatus for treating pathogens by a non-invasive treatment (minimally invasive treatment).

It is also an object of the invention to provide a method/process and apparatus for non-invasive treatment of the Herpes Simplex group of viruses and *Staphylococcus Aureus* ("Golden Staph") bacteria.

BRIEF DESCRIPTION OF THE INVENTION

This invention provides a method/process and apparatus for the non-invasive treatment of micro-organisms within a host's body without damaging the host and can be used to destroy pathogens in both the bacterial and viral groups.

Of particular interest is the treatment against the Herpes Simplex group of viruses, which are the infecting pathogens in genital herpes and oral cold sores. Also, bacteria such as *Staphylococcus Aureus* ("Golden Staph") which can cause major infections in soft tissue and bone.

In one form, the invention relates to a method/process and apparatus for treatment of Herpes Simplex virus I and Herpes Simplex virus II.

According to one aspect of the invention there is provided a method for disrupting or destroying pathogens of at least one selected type located within the body of an organism, said method including the non-invasive administration to pre-selected locations on or in said organism of an amount of low intensity ultrasonic energy, effective to disrupt or destroy the selected pathogens but not deleteriously affect the organism, said low intensity ultrasonic energy falling within a pre-defined range of frequencies and the intensity of said low intensity ultrasonic energy falling within a predefined range of intensity.

The amount of ultrasonic energy provided is a function of the intensity and the period of time for which it is supplied or applied.

It has been found that systems, bodies and entities all have a natural frequency peculiar to that entity. When an entity is exposed to that natural frequency, a rapid increase in vibration and temperature occurs. In the case of structural entities major damage may occur and in the case of a biological entity this damage usually results in the death of a living organism or destruction of a viral particle. [By closely setting the transmitted frequency of the ultrasonic energy, to the natural frequency of the pathogen, there is little or no effect on the surrounding tissue].

Preferably the pathogens are selected from the group consisting of Herpes Simplex Virus I, Herpes Simplex Virus II and Staphylococcus Aureus.

According to another aspect of the invention the said predefined range of frequencies is one or more ranges of frequencies at which the low intensity ultrasonic energy has optimal effectiveness in disrupting or destroying a particular pathogen.

For this specific application the optimum effectiveness in the destruction of the pathogens occurs in the following frequency bands:

| Pathogen | Frequency band |
| --- | --- |
| HSV I | 291-293 kHz and 345-346 kHz |
| HSV II | 353-354 kHz and 362-363 kHz |
| Staph. Aureus | 376-377 kHz and 380-381 kHz |

The method can include the treatment being administered topically over the underlying infection, in the case of *Staphylococcus Aureus*.

The location of treatment can be over the lumbar dorsal ganglia in the case of genital HSV I and HSV II. Alternatively, the location of treatment can be over the trigeminal ganglia of the patient's face.

The invention also provides a method for controlling/preventing future viral growth and replication of Herpes Simplex virus comprising administering to a subject in need of such treatment a treatment comprising applying an effective amount of low intensity ultrasonic energy in a predefined frequency range.

According to another aspect of the invention there is provided an apparatus for disrupting or destroying pathogens of at least one selected type located within the body of an organism, said apparatus including a transducer probe preferably provided with a plate having a surface of a size generally corresponding to a predetermined treatment area of a host to be treated, a generator for the production of low intensity ultrasonic energy, and a means for controlling the intensity of said low intensity ultrasonic energy, and a means for controlling the frequency of the low intensity ultrasonic energy, and power means for powering the apparatus.

Preferably said means for controlling the frequency of the low intensity ultrasonic energy includes means for selecting predefined ranges of said frequencies.

The generator for the production of low intensity ultrasonic energy at a low power range, preferably includes a frequency controller for controlling the frequency of the low intensity ultrasonic energy wherein the frequency of the emitted low intensity ultrasonic energy can be controlled to correspond to a predetermined range of natural frequencies specific to the virus to be treated in its dormant state in the patient. Alternatively, the predetermined natural frequency range is for a bacterium such as *Staphylococcus Aureus*.

The transducer converts electrical energy into vibration energy at ultrasonic frequencies. Low intensity ultrasonic energy preferably of 30 mW/cm$^2$ is substantially uniformly produced over the surface area of the transducer probe or transducer plate preferably in 'bursts' of 200 microseconds on and 800 microseconds off. The transmitting surface area of the transducer is intended to cover the entire area being targeted by the ultrasound waves. The surface area of the transducer probe or plate typically is 120 cm$^2$ (80 mm×150 mm).

The generator produces the predetermined waveform, frequency and amplitude of the signal. The signal is then amplified by a power amplifier. The amplifier output is impedance matched to the ultrasonic transducer to ensure maximum power transfer. The transducer converts the received electrical energy into vibration energy at ultrasonic frequencies. The resulting low intensity ultrasonic energy is substantially uniformly transmitted from the whole surface of the piezo electric ceramic plate.

The ultrasonic energy is produced in bursts at the selected frequency, that have a preferred duty cycle of 20%. The term duty cycle number indicates the proportion of the cycle during which ultrasonic energy is applied. Duty cycle is defined as the ratio of the "burst" ON time to the time of one cycle× 100. One cycle being the sum of the "burst" ON time and the OFF time:

$$\text{Duty Cycle} = \frac{\text{"Burst" ON time}}{\text{"Burst" ON time} + \text{OFF time}} \times 100$$

The preferred cycle is a "burst" duration of 200 microseconds ON followed by a period of OFF time for 800 microseconds. The "burst" ON time and the OFF time can be varied to achieve a desired effect while still remaining within safety margins, and maintain the preferred duty cycle of 20% (e.g., 100 microseconds ON and 400 microseconds OFF also represents a 20% duty cycle). The provision of burst of ultrasonic energy is intended to prevent heat and mechanical damage to the target zone thus ensuring patient safety.

The transducer surface is matched to the area being treated in each separate case to cover the target area adequately for greater efficiency.

For the treatment of the dorsal ganglia area a large transducer covers the base of the spine.

For the treatment of the trigeminal ganglia area the transducer covers the mid third of the face.

For the treatment of *Staphylococcus Aureus* various different sized transducers can be used depending on the size and site of the infection.

In the use of the apparatus, a contact gel is applied to the surface of the skin of a host or patient, and the transducer probe is applied to the skin area covered by the gel. The generator is set to the required range of frequencies determined to be effective for the pathogen to be treated, and the means for controlling the intensity of the low intensity ultrasonic energy is, by adjusting the amplitude of the generator. The apparatus is powered up and the ultrasonic energy is applied for a predetermined period of time so that a predetermined amount of energy is transmitted to the target area.

Still further the invention provides a method of treatment including the steps of:

a) providing an ultrasonic transducer corresponding in size and shape to the patient's treatment area for a stationary fixed position, one-step treatment process;

b) energy at the predetermined frequency within the predetermined range of frequencies for the pathogen to be treated is applied to the transducer which emits the ultrasonic energy at the applied frequency into the body of the patient;

c) the location of application of the transducer is determined by the underlying target area. The area is then treated with the ultrasonic energy at the selected transmitted frequency to obtain destruction or disruption of the target organism where it lies in a dormant state;

d) the generator provides the frequency, waveform and amplitude of the signal which is then amplified via the power amplifier. The output power is then converted by the transducer to ultrasonic energy and then is transmitted into the body for the predetermined amount of time.

The transducer probe is placed on the skin with an interface of conducting gel over the base of the lumbar spine in order to treat the virus in its dormant or semi dormant state at the lumbar dorsal ganglia where, in particular, it has been found that HSV I and II lie dormant.

The predetermined time period over which treatment is applied to the treatment area can be for up to 20 minutes. However, the predetermined time period can vary between 3 minutes 20 seconds and up to 20 minutes, with a preferred range being between 3 minutes 20 seconds and 10 minutes.

This invention is intended to selectively destroy pathogens in the viral and bacterial range in a human or animal body without affecting normal body function and without destroying or damaging normal body structures.

In particular this system provides for a non-invasive treatment of viruses whilst they lie dormant in the lumbar dorsal ganglia, the sacral ganglia and the trigeminal ganglia.

This invention also relates to a method and apparatus for the non-invasive treatment of bacteria. In particular it relates to a method and apparatus for treatment of *Staphylococcus Aureus*, which is a causative pathogen in severe bodily infections. *Staphylococcus Aureus* is found on the skin and inside the nose. This bacterium is usually harmless but has the potential to cause serious infection and illness, which may lead to death. The elderly and very ill are most at risk. Some strains of this bacterium have developed resistance to most antibiotics and have become very difficult to treat.

It has been found that all living organisms have a natural frequency. When an organism has been exposed to energy at its 'natural frequency', from an 'external power source' a rapid increase in vibration and temperature occurs. In the case of a living organism this usually results in the death of that organism. By closely setting the frequency of the applied energy to the natural frequency of the organism, in this case a pathogen within another organism, there is little or no effect on the surrounding tissue and other organisms.

Thus the invention also provides a method of treating *Staphylococcus Aureus*. Frequencies within a predetermined frequency range are produced by a generator and amplified by a dedicated power amplifier and the resulting low intensity ultrasonic energy is then transmitted to the treatment area via a transducer. It is to be understood that a reference to a frequency includes a reference to a frequency with an accepted tolerance.

The method of treatment according to this aspect of the invention includes using frequencies substantially in the range of 376-377 kHz and 380-381 kHz.

The treatment has the following steps:

A transducer is placed over the infected area, using an interface of conducting gel. The generator is set to a frequency within a predetermined frequency range for *Staphylococcus Aureus*, and the ultrasonic energy is output in bursts at the set frequency, that have a duty cycle of 20%. This indicates that the ultrasonic energy is applied for 20% of the one cycle and is then repeated. The preferred duty cycle for treatment is 200 microseconds ON and 800 microseconds OFF: thus;

$$\text{Duty Cycle} = \frac{200}{200+800} \times 100 = 20\%$$

The burst ON time and OFF time may be set to best suit the application and maintain a 20% duty cycle (e.g., 2 milliseconds ON and 8 milliseconds OFF also is a 20% duty cycle). The amplitude of the signal from the generator is set to the level, at the frequency being used to correspond to a particular power output, preferably of 3.6 W, when amplified by the dedicated power amplifier. This corresponds to an ultrasonic intensity of 30 mW/cm$^2$ at a transducer plate having a surface area of 120 cm$^2$. The treatment is applied preferably for a period of ten minutes (standard treatment) but time and power can be varied as necessary. In some instances the ultrasonic intensity can be increased to 40 mW/cm$^2$. In some instances two ten minute sessions can be used.

The values of the minimum intensity level, burst ratio, "on" pulse duration, and treatment time of the applied ultrasonic energy determined to produce the optimum effect in the destruction or disruption of the pathogen will be the set values for each parameter. Once determined, these parameters may have values that are higher or lower than the specified preferred values of these parameters. The minimum intensity level will be set within the predefined intensity range of 10 mW/cm$^2$ to 100 mW/cm$^2$.

It will be appreciated that treating pathogens using chemical methods, such as antibiotics, antivirals, or other chemical agents can have side effects. It can be appreciated that since chemical agents are not used in the present method such side effects are not encountered.

It can also be appreciated that since chemicals are not used, there is not an increase in resistance to the treatment such as occurs when treating with antibiotics, antivirals and other chemical agents.

This process/method provides a non-invasive, method of treatment including the steps of:

application of contact gel to the target area followed by positioning of the transducer on the contact gel;

selection of the appropriate frequency and amplitude and initiation of the treatment;

the ultrasonic energy of selected frequency being transmitted at low intensity and at a preferred duty cycle of 200 microseconds on and 800 microseconds off;

an optimum effect is obtained by closely setting the frequency of the transmitted ultrasonic energy to the natural frequency of the target pathogen;

the intensity of the ultrasonic energy output from the transducer surface, preferably is set at 30 mW/cm$^2$, which can be varied as required.

This process may be used to selectively treat HSV I and II in the lumbar area, HSV I and II in the facial area, and *Staphylococcus Aureus* in various target areas of the body of the patient.

For HSV I and II the standard treatment time is 10 minutes but can be varied. A preferred range of treatment time is between 3 minutes 20 seconds and 10 minutes.

For *Staphylococcus Aureus* the preferred treatment time is 10 minutes but this may be increased up to 20 minutes per session.

While usually one treatment will suffice, multiple treatment sessions may be required.

The transducer transmits ultrasonic energy into the body of the host at low intensity and the ultrasonic energy is pulsed to minimise or prevent any thermal or mechanical bio effects on body tissue, bone and cells. This allows the transducer to remain stationary over the target area for the duration of the treatment.

When treating the Herpes Simplex viruses I and II, the sizes and shapes of the transducers are designed to cover the target areas of the respective ganglia (dorsal, sacral and trigeminal). The respective transducer can therefore remain stationary during the treatment. However, the treatment area for HSV I and HSV II, located in the region of the lumbar dorsal ganglia, exceeds the area covered by the large transducer plate. Accordingly, when treating the target area for HSV I and HSV II the transducer plate is held stationary on a first treatment location (preferably in the region of the kidneys) for the duration of the treatment period and then is moved to an overlapping further treatment location (preferably further down the spine) for administration of further treatment for a further treatment period. This process is repeated until the entire target area of the lumbar dorsal ganglia is covered. When treating *Staphylococcus Aureus* bacteria, the size and shape of the transducers used depends on the size and site of the infection. For large chronic infections, overlapping areas may be treated. The transducer remains stationary on a first treatment location for the duration of the treatment period and is then moved to an overlapping further treatment location for administration of a similar treatment. However, different transducers may be required to treat the infected areas depending on the location of the infection on the body of the host.

In the case of HSV I and HSV II the specifically selected treatment results in the destruction or disruption of the dormant virus particles thus preventing a new infection travelling down the peripheral nerves from the ganglia.

In the case of *Staphylococcus Aureus* the specifically selected treatment results in the destruction or disruption of the bacteria and allows effective healing more rapidly and with reduced scarring.

The invention provides a non-complex method of treatment for the destruction or disruption of specific viruses or a bacterium. It can be used in hospitals, clinics and doctors' surgeries, as it is easy to use and is non-invasive, thereby offering minimal discomfort to the patient being treated.

BRIEF DESCRIPTION OF THE DRAWINGS

In order for the invention to be more readily understood an embodiment will be described by way of illustration only with reference to the drawings wherein.

DESCRIPTION OF AN EMBODIMENT OF THE INVENTION

Figure 1:
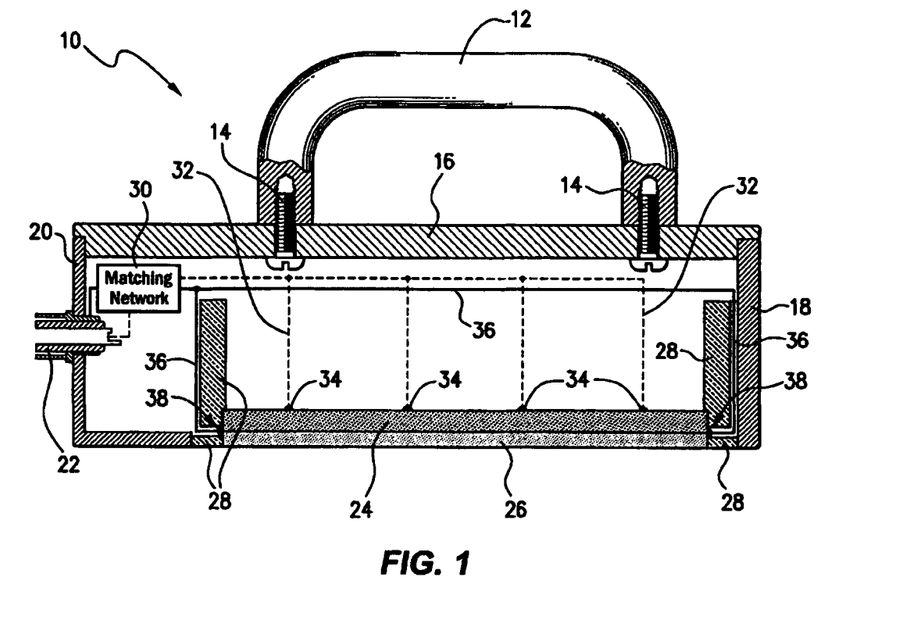
FIG. 1 is a cross-sectional view of a large area ultrasonic transducer in accordance with an embodiment of the invention.
Figure 2:
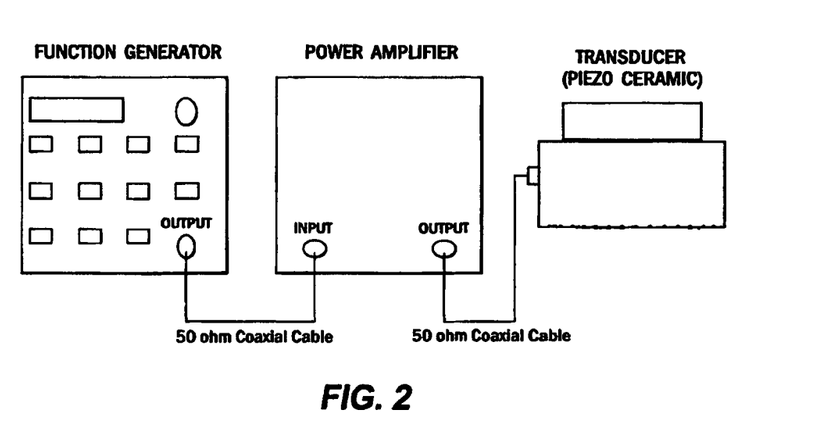
FIG. 2 is a system diagram of an embodiment of the system for treatment of applying a determined range of natural frequencies for viral or bacterial infections according to the invention.

FIG. 1 shows a cross-sectional view of a large area ultrasonic transducer for use in the method of treatment. This transducer is sized to correspond with the patient treatment area for a fixed one step treatment process. In particular the size of the transducer piezo electric ceramic plate is about 80 by 150 mm.

The transducer identified generally by the numeral 10 comprises a U-shaped handle 12 attached securely by screws 14 to the lid 16 of a housing 18, constructed from machined aluminium pieces. The U-shaped handle permits easy handling of the transducer. One side wall 20 is provided with a mounting for a bulk head UHF connector 22. The housing contains a 800 kHz piezo electric ceramic plate 24 the lower surface of which is covered by a cast tungsten/epoxy matching layer 26 lapped down to give optimum performance. The plate 24 and matching layer 26 are mounted at the lower end of a hollow insulating block 28 machined from clear Perspex. The UHF connector 22 extending through the side wall of the housing allows infeed of low power frequencies provided at the required frequencies by a frequency generator and power amplifier (not shown). The connector 22 is connected to an internal matched network 30 including live wires 32 connected to spaced VE contacts 34 on the internal back of the piezo electric ceramic plate. Other electrode connectors include GND wires 36 soldered onto the piezo electric ceramic plate 24 and the matching layer 26 at up to 8 points 38 (not all shown) and which complete the circuit back to the matching network.

The transducer shown in cross-sectional view in FIG. 1 is specifically designed for application to the lower sacral spinal area for the treatment of the viruses that give rise to genital herpes in both male and female patients. However, it can be used for application to other large flat and substantially flat surface infections such as those due to *Staphylococcus Aureus*. Differently dimensioned and shaped transducers specific for other parts of the body of a patient are envisaged. Typically they will have a handle similar to that shown in FIG. 1, but the surface area of the piezo electric ceramic plate and base plate will differ in size and shape. For example, a differently sized and shaped transducer will be required for targeting the trigeminal ganglia of the face.

The transducer's preferred operating intensity is 30 mW/cm$^2$, with spatial peak intensity of 65 mW/cm$^2$. If one assumes that the transducer intensity is completely uniform across its face the total power can be calculated from the product of the transducer area and the required intensity.

| Intensity (mW/cm$^2$) | Transducer Width (mm) | Transducer Length (mm) | Area (cm$^2$) | Power (W) |
|---|---|---|---|---|
| 30 | 80 | 150 | 120 | 3.60 |
| 65 | 80 | 150 | 120 | 7.80 |

In practice there will be some deviation from the uniform output over the transducer face because of edge wave interactions, but these effects will be localised and the area average is likely to be consistent with the above calculations.

Figure 3:
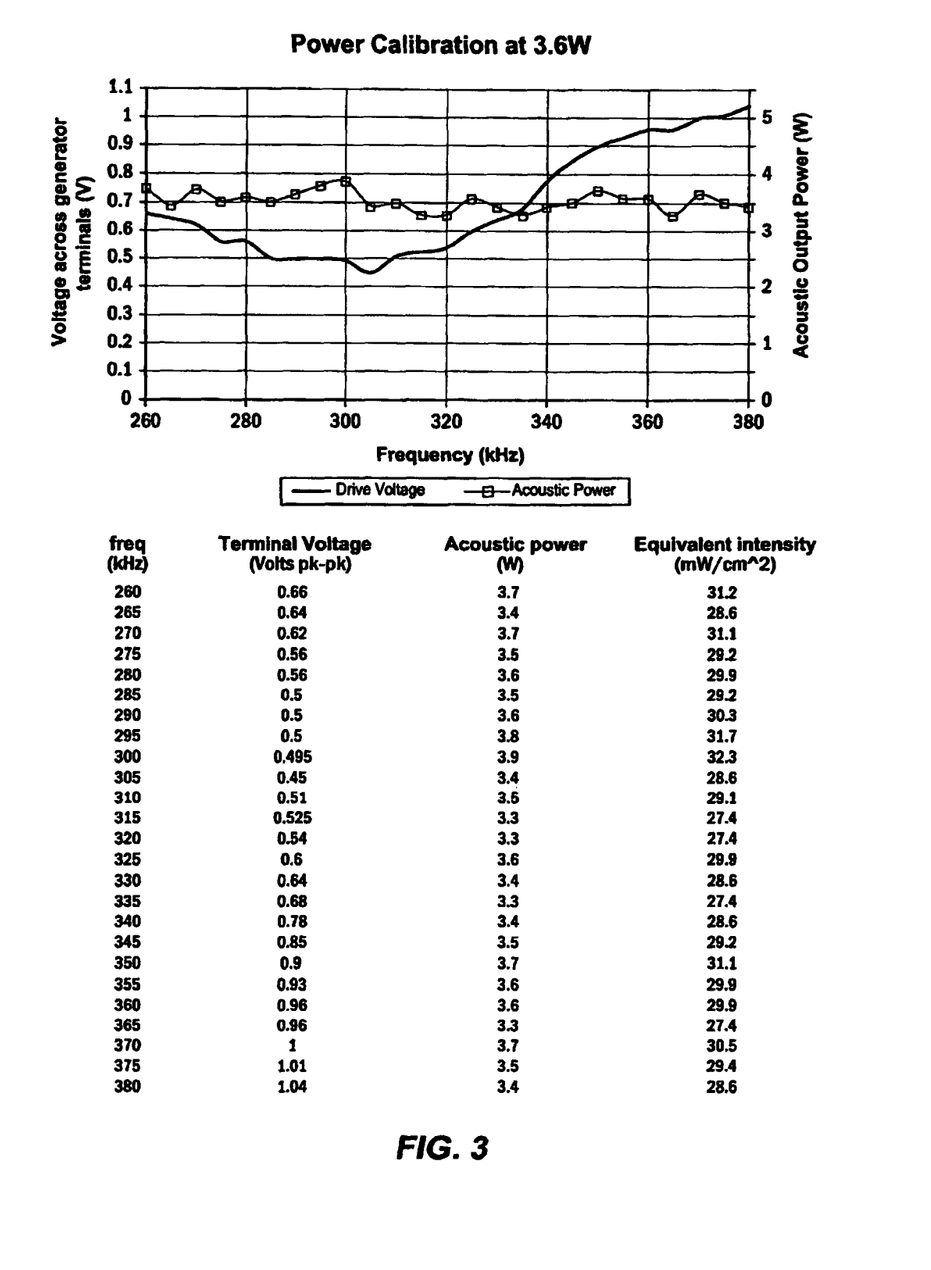
FIGS. 3 and 4 are power calibration charts showing attuning of power across a transducer to provide an effective constant low intensity ultrasonic energy output over the defined frequency range for use in an embodiment of the system for treatment of applying a range of determined natural frequencies for viral or bacterial infections according to an embodiment of the invention.
Figure 4:
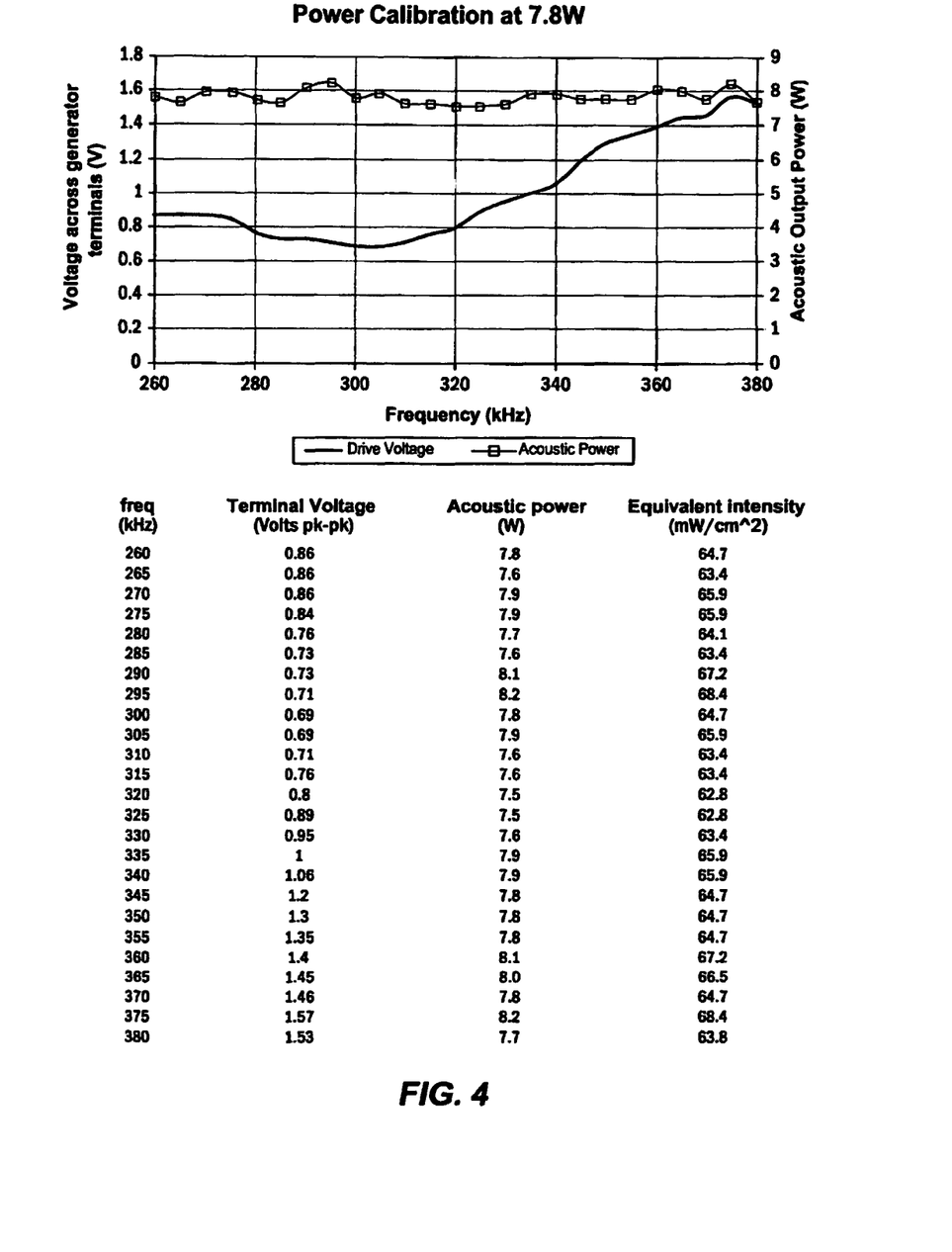

The power amplifier and transducer combination produce an output intensity that varies as a function of frequency as shown in the calibration charts in FIGS. 3 and 4. To maintain an output intensity at a substantially constant level across the operating frequency range of the piezo electric ceramic plate, the drive amplitude of the generator was adjusted so that the measured intensity, determined by a radiation force balance, are consistent with the intensities listed in FIGS. 3 and 4.

The generator peak to peak voltages were measured with an oscilloscope probe at the input of the amplifier. These are recorded in both table form and as a graph, as a function of frequency along with the recorded output acoustic power for both intensity levels.

The generator is set to a frequency within the frequency ranges:

1. For the viruses HSV I and HSV II substantially in the ranges of 291 to 293 kHz and 345 to 346 kHz; and 353 to 354 kHz and 362 to 363 kHz, respectively;

2. For the *Staphylococcus Aureus* ("Golden Staph"), substantially in the ranges of 376 to 377 kHz and 380 to 381 kHz.

For viral infections HSV I and HSV II, the location at which the transducer is placed on the patient's body is determined by anatomical landmarks, which indicate/suggest where the virus particles reside most likely when dormant.

Due to the application of the low intensity ultrasonic energy transmitted, within the prescribed frequency range and predetermined treatment time, the overall low intensity of energy applied offers significantly reduced or minimal risk to the patient.

The transducer is placed on the skin with an interfacing layer of conducting gel over the base of the lumbar spine in order to treat the virus in its dormant or semi dormant state within the lumbar dorsal ganglia where, in particular, it has been found that HSV I and II lie dormant (in the case of genital herpes).

In general, because herpes viruses live inside the body cells they are difficult to destroy without harming the host.

It has been found that systems, bodies and entities all have a natural frequency peculiar to that entity. When an entity is exposed to that natural frequency, a rapid increase in vibration and temperature occurs. In the case of structural entities major damage may occur and in the case of a biological entity this damage usually results in the death of a living organism or destruction of a viral particle.

The invention provides a method of destroying/disrupting HSV I and HSV II particles in their dormant state.

The generator produces signals at specific frequencies and waveforms that are amplified by the dedicated power amplifier. The energy is then transmitted to a custom built transducer specifically designed for this particular medical condition, which is then applied:

1. to the lower lumbar skin overlying the dorsal ganglia in the lower lumbar spine/sacral spine area in the case of treating HSV I and HSV II causing genital herpes;
2. to the facial skin overlying the trigeminal ganglia in case of the HSV I and HSV II causing lip and peri oral herpes.

The method of treatment includes using frequencies substantially in the range of:

291 to 293 kHz and 345 to 346 kHz for HSV (1) and 353 to 354 kHz and 362-363 kHz for HSV (2), respectively.

The treatment has the following steps:

(i) The power amplifier is switched on and allowed to stabilise;
(ii) The generator is set for the required waveform, frequency and amplitude, and pulse duration is set to the preferred duty cycle of 200 microseconds on and 800 microseconds off (which may be varied);
(iii) An interface of conducting gel is spread over the target surface area of the skin of the patient, in this instance in the region of the lower lumbar spine overlying the dorsal ganglia as described earlier. The transducer is then placed on the skin in contact with the interface of conducting gel;
(iv) The main switch of the generator is turned on to apply the ultrasonic energy;
(v) When the predetermined treatment time has elapsed the generator is turned off and the transducer is removed and cleaned for further use.

For this specific application the optimum effectiveness in the destruction of the pathogens occurs in the following frequency bands:

| Pathogen | Frequency band |
| --- | --- |
| HSV I | 291-293 kHz and 345-346 kHz |
| HSV II | 353-354 kHz and 362-363 kHz |
| Staphylococcus Aureus | 376-377 kHz and 380-381 kHz |

Testing of Method/Apparatus in Laboratory
Test 1 (Viral)

The virus used in the test is called Lambda.

This organism is specific in infecting a particular strain of *Escherichia Coli*, which is used as the host in testing.

A basic description of the test method is as follows:

The Lambda bacteriophage is placed in a 3 ml syringe, which is then placed into the marrow of a beef bone surrounded by its meat. The bone and its surrounding meat is then placed into a container encapsulating it in gelatine. The meat and bone sample containing the syringe undergoes the "treatment process". On completion of the treatment a sample from the syringe is extracted and then distributed onto sloppy agar, which contains the *E. Coli* host. After incubation the virus is detected by the formation of plaques and these plaques are counted.

The experiment showed a viral (lambda) kill of 98.39% after 3 mins, 20 secs and 99.97% kill after 10 minutes of treatment.

1. a 100% death of the virus is indicated by a count of zero plaques
2. a 0% death of the virus is indicated by a count of 100% plaques.

Test 2 (Bacterial)

In a test of the system and method in relation to bacteria a 3 ml syringe of *Staphylococcus Aureus* was placed into the marrow of a beef bone containing a covering of meat which in turn was covered with gelatine in order to simulate a bacterial infection in a bone area and being treated externally through a thickness of tissue and muscle. The meat and bone sample containing the syringe undergoes the "treatment process". On completion of the treatment a sample from the syringe is extracted and distributed onto laboratory plates.

With the application of low intensity ultrasonic energy and set frequencies in the range of 376 to 381 kHz for treatment times of 3 mins 20 secs and 10 mins the following results were obtained.

Indicative Results

| Ultrasonic intensity applied is 30 mW/cm$^2$ | | | | | |
| --- | --- | --- | --- | --- | --- |
| Sample | Time applied | No's destroyed | No's remaining | % Destroy | % Remain |
| A | 3 m 20 s | $1.09324 \times 10^9$ cfu/ml | $6.760 \times 10^6$ cfu/ml | 99.385% | 0.615% |
| A | 10 m | $1.0954510^9$ cfu/ml | $4.550 \times 10^6$ cfu/ml | 99.586% | 0.414% |

| Ultrasonic intensity applied is 20 mW/cm$^2$ | | | | | |
| --- | --- | --- | --- | --- | --- |
| Sample | Time applied | No's destroyed | No's remaining | % Destroy | % Remain |
| B | 3 m 20 s | $1.0746 \times 10^9$ cfu/ml | $2.546 \times 10^7$ cfu/ml | 97.69% | 2.31% |
| B | 10 m | $1.0802 \times 10^9$ cfu/ml | $1.981 \times 10^7$ cfu/ml | 98.20% | 1.8% |

It can be seen that an effective destruction rate of the bacteria is achieved by treating at an effective low intensity ultrasonic energy level.

The bacterium used for the tests was a laboratory strain of *Staphylococcus Aureus*.

Tests for Ultrasound Safety

Trials on pigs were conducted to ascertain the safety of exposure to ultrasound energy. Pigs were exposed to ultrasonic energy at various intensities to observe the effects, if any, on the nerves which control the musculo-skeletal system of the animal. The pigs were exposed to ultrasonic energy over the spine, in the lumbar region, of the animals.

Test Method

Six (6) pigs were exposed to ultrasonic energy at various intensities, waveforms and duty cycles. Another six (6) pigs were used as a control group. These were not exposed to ultrasonic energy. The control group was used as a control group of reference, to identify any bio effects that may have occurred in the group of pigs exposed to ultrasonic energy. The ultrasonic transducer was placed over the spine in the lumbar region of six(6) pigs with an interface of conducting gel.

The ultrasound exposure conditions are set out in Table 1.

TABLE 1

| Pig I.D. | Intensity applied | Wave- form | Duty Cycle Continuous - | Pulse on-off | Expo- sure time |
|---|---|---|---|---|---|
| Silver | 65 mW/cm2 | Square | continuous | | 10 min |
| Red | 65 mW/cm2 | Square | | 2 mS-8 mS | 10 min |
| Blue | 65 mW/cm2 | Sine | | 20 µS-800 µS | 10 min |
| Green | 30 mW/cm2 | Square | continuous | | 10 min |
| Yellow | 30 mW/cm2 | Square | | 2 mS-8 mS | 10 min |
| White | 30 mW/cm2 | Sine | | 200 µS-800 µS | 10 min |

Test Results

All pigs were observed over a period of four (4) months. The pigs exposed to the ultrasonic energy showed no evidence of musculo-skeletal effects, when compared to the control group.

The pigs in both the control group and the group exposed to the ultrasonic energy were slaughtered. A sample of the spinal cord of each animal was examined by a veterinary pathologist to determine whether any cell damage occurred, from exposure to the ultrasonic energy. All samples of the spinal cord were supplied unidentified. The findings of the pathologist were that the cells in both the control and exposure groups, showed no evidence of cell damage. Images of cells examined with a laboratory microscope showed all samples of spinal cord supplied were consistent with normal cells.

Human Test Results

Trials have been conducted on human patients at their respective targeted sites, using the method of treatment as outlined in this specification.

The results of the trials indicate that the method of treatment devised/applied is effective in the destruction or disruption of the targeted pathogen. Furthermore no side effects or ill effects to the patients treated have been presented or observed clinically.

Staphylococcus Tests

Suspected *Staphylococcus Aureus* bacterial skin infection was submitted and confirmed by pathology laboratory.

A patient presenting with *Staphylococcus Aureus* infection MRSA of 9 months duration was treated by a method according to the present invention at the site of the infection. The result of the treatment indicated that the method of treatment devised was effective in the destruction or disruption of the said pathogen. 18 months later there has been no recurrence. The site of infection in the patient healed and the associated pain in the treated area was also relieved. No side or ill effects have been reported. Clinical observations have also confirmed this.

HSV I and HSV II Tests

The human patients presented for treatment were confirmed by pathology laboratories to have acquired HSV I or HSV 2 (HSV Herpes Simplex virus). Patients for treatment were selected from individuals who suffered monthly or very frequent regular (outbreak) episodes. The patients were treated at targeted sites according to the methods outlined in this specification. The results of the treatments indicated that the method of treatment was effective in the disruption/destruction of the said pathogens. The tests also revealed that the patients who suffered from monthly outbreaks reported the regular monthly outbreak cycle did not represent with the same symptoms. The patients treated have reported no side or ill effects. Clinical observations have also confirmed this.

It should be understood that the above description is of a preferred embodiment and included as illustration only. It is not limiting of the invention. Clearly variations of the method and apparatus for a non-invasive treatment of viruses would be understood by a person skilled in the art without any inventiveness and such variations are included within the scope of this invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference to any prior art in this specification is not, and should not, be taken as an acknowledgment or any form or suggestion that the prior art forms part of the common general knowledge in Australia or elsewhere.

The invention claimed is:

1. A method for disrupting or destroying selected pathogens selected from the group comprising Herpes Simplex virus I, Herpes Simplex virus II, and *Staphylococcus Aureus* located within the body of an organism including the steps of:
   selecting a pathogen to be disrupted, with each pathogen being subjected to intensity of a low intensity ultrasonic energy to a value distribution substantially limited within predefined ranges of frequencies, wherein the predefined ranges of frequencies are: 291 to 293 kHz and 345 to 346 kHz, where a selected pathogen is Herpes Simplex virus I; 353 to 354 kHz and 362 to 363 kHz, where a selected pathogen is Herpes Simplex virus II; and 376 to 377 kHz and 380 to 381 kHz, where a selected pathogen is *Staphylococcus Aureus*,
   non-invasively administering an amount of the low intensity ultrasonic energy to a treatment location on or in the organism, wherein the treatment location is a ganglia, where the selected pathogen is Herpes Simplex viruses I or II or a site of infection, where the selected pathogen is *Staphylococcus Aureus*, and
   disrupting or destroying the selected pathogen while not deleteriously affecting the organism.

2. The method of claim 1, wherein the intensity of the low intensity ultrasonic energy is within a range of 10 mW/cm$^2$ to 100 mW/cm$^2$.

3. The method of claim 1, wherein administering the low intensity ultrasonic energy occurs in bursts that have a 20% duty cycle.

4. The method of claim 1, wherein total time of administration allows for maximum disruption or destruction of the selected pathogens, but does not deleteriously affect tissue of the organism surrounding the selected pathogens.

5. An apparatus for disrupting or destroying pathogens of at least one selected pathogen type selected from the group comprising Herpes Simplex virus I, Herpes Simplex virus II, and *Staphylococcus Aureus* located within the body of an organism including:
   a transducer probe provided with a plate having a surface of a size corresponding to a treatment area of a host to be treated, wherein the treatment area is a ganglia, where a selected pathogen is Herpes Simplex viruses I or II or a site of infection, where the selected pathogen is *Staphylococcus Aureus*, a generator configured to produce low intensity ultrasonic energy for delivering to the body of the organism, having one of a plurality of predefined substantially limited ranges of frequencies associated with a selected pathogen type, a power amplifier, wherein a combination of the transducer and the power amplifier configured to produce the intensity of the low intensity ultrasonic energy, wherein the combination of the transducer, the power amplifier and the generator produce the selected low intensity ultrasonic energy and the frequency specific to the pathogen and, wherein the generator controls the frequency and intensity, of the low intensity ultrasonic energy administered, and the power amplifier powers the generator, and wherein the generator combined with a UHF connector control a frequency of the low intensity ultrasonic energy administered, wherein the predefined ranges of frequencies are: 291 to 293 kHz, and 345 to 346 kHz, where the selected pathogen is Herpes Simplex virus I, 353 to 354 kHz and 362 to 363 kHz, where the selected pathogen is Herpes Simplex virus II, and 376 to 377 kHz and 380 to 381 kHz, where the selected pathogen is *Staphylococcus Aureus*.

6. The apparatus of claim 5, wherein the generator combined with the UHF connector enables selection of the low intensity ultrasonic energy to a value within the predefined ranges of frequencies.

7. The apparatus of claim 5, wherein the intensity of the low intensity ultrasonic energy is within a range of 10 mW/cm$^2$ to 100 mW/cm$^2$.

8. The apparatus of claim 5, wherein the low intensity ultrasonic energy is produced in bursts that have a 20% duty cycle.

9. The apparatus of claim 8, wherein the duty cycle is about 200 microseconds ON and 800 microseconds OFF.

10. The method of claim 3, wherein the duty cycle is about 200 microseconds ON and 800 microseconds OFF.

\* \* \* \* \*